(12) United States Patent
Jahns

(10) Patent No.: US 8,445,066 B2
(45) Date of Patent: May 21, 2013

(54) SYSTEMS AND METHODS FOR MAKING MONOLITHIC GEL BODIES

(75) Inventor: Michael Jahns, Gilching (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/512,075

(22) PCT Filed: Dec. 9, 2010

(86) PCT No.: PCT/US2010/059598
§ 371 (c)(1),
(2), (4) Date: May 25, 2012

(87) PCT Pub. No.: WO2011/075370
PCT Pub. Date: Jun. 23, 2011

(65) Prior Publication Data
US 2012/0276295 A1    Nov. 1, 2012

Related U.S. Application Data

(60) Provisional application No. 61/287,721, filed on Dec. 18, 2009.

(51) Int. Cl.
*B05D 3/10*    (2006.01)

(52) U.S. Cl.
USPC ..... 427/335; 427/377; 427/419.1; 427/419.2; 427/419.6

(58) Field of Classification Search
None
See application file for complete search history.

(56) References Cited

U.S. PATENT DOCUMENTS

| 4,919,871 | A | * | 4/1990 | Lin et al. ........................ 264/82 |
| 4,925,647 | A | * | 5/1990 | Kirchhofer ................ 423/592.1 |
| 5,076,980 | A |   | 12/1991 | Nogues |
| 5,368,887 | A | * | 11/1994 | Hoshino et al. ................ 427/226 |
| 5,420,086 | A | * | 5/1995 | Brandau et al. ................ 501/103 |
| 6,063,714 | A | * | 5/2000 | Smith et al. .................... 438/778 |
| 6,156,685 | A |   | 12/2000 | Marella |
| 6,319,852 | B1 | * | 11/2001 | Smith et al. .................... 438/778 |

(Continued)

FOREIGN PATENT DOCUMENTS

| EP | 0461782 | 12/1991 |
| JP | 4160020 | 6/1992 |
| WO | WO 2006/120387 | 11/2006 |

OTHER PUBLICATIONS

Vogel et al., "Postsynthesis Stabilization of Free-standing Mesoporous Silica Films" vol. 20, 2004, pp. 2908-2914.
International Search Report PCT/US2010/059598, Mar. 18, 2011, 3 pages.
Gupta et al., "Bioactive materials for biomedical applications using sol-gel technology" Biomed. Mater. 3 (2008) 15 pp.

(Continued)

*Primary Examiner* — Erma Cameron
(74) *Attorney, Agent, or Firm* — Nicole J. Einerson

(57) ABSTRACT

Systems and methods for making a monolithic gel body. Some systems can include a substrate, a sol, an ammonia atmosphere. Some methods can include applying a first quantity of the sol to the substrate to form a first coated substrate, and positioning the first coated substrate in the ammonia atmosphere to cure the first quantity of sol to form a first supported gel comprising a first gel supported by the substrate. Such methods can further include applying a second quantity of the sol to the first supported gel to form a second coated substrate comprising the second quantity of sol and the first supported gel. Some methods can include positioning the substrate in the ammonia atmosphere while applying the sol onto the substrate to form a monolithic gel body by a layering process.

21 Claims, 4 Drawing Sheets

U.S. PATENT DOCUMENTS

| | | | |
|---|---|---|---|
| 6,387,453 B1 * | 5/2002 | Brinker et al. | 427/387 |
| 6,784,121 B1 | 8/2004 | Jin | |
| 7,919,145 B2 * | 4/2011 | Meredith et al. | 427/335 |
| 2004/0179800 A1 * | 9/2004 | Walker et al. | 385/128 |
| 2007/0065699 A1 * | 3/2007 | Larson et al. | 429/33 |
| 2007/0089642 A1 | 4/2007 | Engler | |
| 2007/0245772 A1 | 10/2007 | Lieberman | |
| 2009/0004371 A1 | 1/2009 | Johnson | |
| 2009/0311650 A1 | 12/2009 | Stephan | |
| 2011/0151411 A1 | 6/2011 | Schechner | |

OTHER PUBLICATIONS

Caruso et al., "Controlled preparation and characterization of multilayer sol-gel zirconia dip-coatings", J. Mater. Res., vol. 16, No. 8, Aug. 2001, 2391-2398.

Bermejo et al., "Processing optimisation and fracture behaviour of layered ceramic composites with highly compressive layers", Composites Science and Technology 67 (2007) 1930-1938.

Reuter, "Sol-Gel Processes II**:Investigation and Application", Advanced Materials 3 (1991) No. 11, 568-571.

* cited by examiner

SYSTEMS AND METHODS FOR MAKING MONOLITHIC GEL BODIES

RELATED APPLICATIONS

This is a national stage filing under 35 U.S.C. 371 of PCT/US2010/059598, filed Dec. 9, 2010, which claims priority to U.S. Provisional Application No. 61/287,721, filed Dec. 18, 2009, the disclosure of which is incorporated by reference in its entirety herein.

FIELD

The present disclosure generally relates to systems and methods for making monolithic gel bodies, and particularly, for making monolithic gel bodies by a sol-gel reaction.

BACKGROUND

Sol-gel reactions can be used to form glass films, layers or molded articles. Such sol-gel reactions can include hydrolysis and polycondensation of sol-gel precursors, such as metal alkoxides and/or metal chlorides, to form a colloid, or sol. The sol can then evolve toward the formation of an inorganic continuous network containing a liquid phase (gel), which can then be dried to form a porous material. The porous material can then be thermally treated (e.g., fired) to promote further polycondensation and densification and enhance mechanical properties.

SUMMARY

Some aspects of the present disclosure provide a method for making a monolithic gel body. The method can include providing a substrate, providing a sol, and providing an ammonia atmosphere. The method can further include applying a first quantity of the sol to the substrate to form a first coated substrate, and positioning the first coated substrate in the ammonia atmosphere to cure the first quantity of sol to form a first supported gel comprising a first gel supported by the substrate. The method can further include applying a second quantity of the sol to the first supported gel to form a second coated substrate comprising the second quantity of sol and the first supported gel.

Some aspects of the present disclosure provide a method for making a monolithic gel body. The method can include providing a substrate, providing a sol, and providing an ammonia atmosphere. The method can further include dipping the substrate in the sol, and removing the substrate from the sol to form a first coated substrate comprising a first coating of sol on the substrate. The method can further include positioning the first coated substrate in the ammonia atmosphere to cure the first coating of sol to form a first supported gel comprising a first gel supported by the substrate. The method can further include dipping the first supported gel in the sol, and removing the first supported gel from the sol to form a second coated substrate comprising a second coating of sol on the first supported gel.

Some aspects of the present disclosure provide yet another method for making a monolithic gel body. The method can include providing a substrate, providing a sol, and providing an ammonia atmosphere. The method can further include positioning the substrate in the ammonia atmosphere while applying the sol onto the substrate to form a monolithic gel body by a layering process.

Other features and aspects of the present disclosure will become apparent by consideration of the detailed description and accompanying drawings.

DETAILED DESCRIPTION

Figure 1:
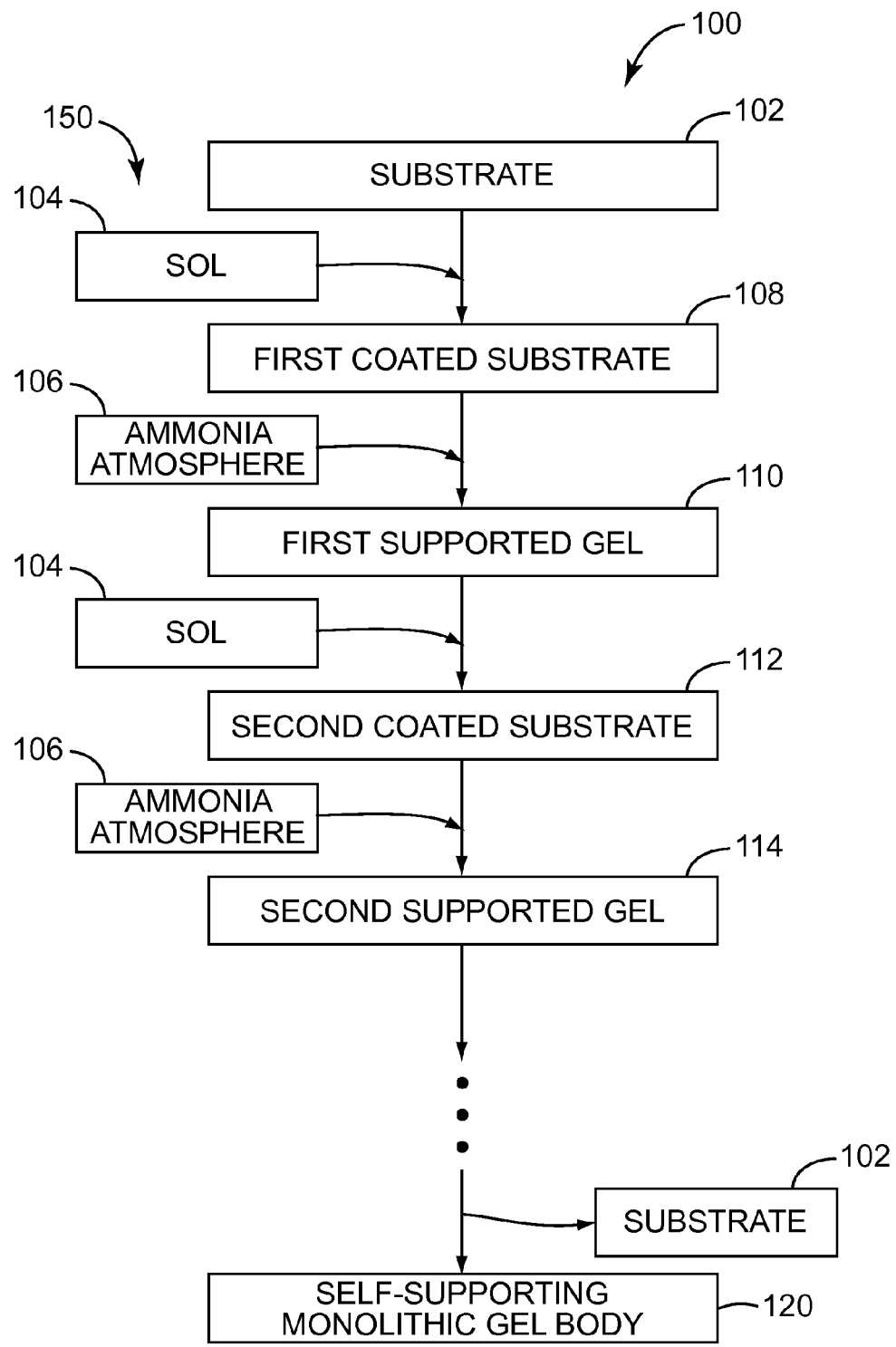
FIG. 1 is a flowchart illustrating a method according to one embodiment of the present disclosure and a system according to one embodiment of the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports, and couplings. Further, "connected" and "coupled" are not restricted to physical or mechanical connections or couplings. It is to be understood that other embodiments may be utilized, and structural or logical changes may be made without departing from the scope of the present disclosure.

The present disclosure generally relates to methods for making substantially crack-free, three-dimensional, monolithic gel bodies that can be used in, or further modified for use in, dental applications. Such gel bodies can be useful in dental applications, for example, as a green body that can be further calcined, machined, and/or fired to produce a dental appliance or a component of a dental appliance.

The phrase "substantially crack-free" is used to generally refer to a gel body that has no visible cracks in its usable volume. That is, in some embodiments, the gel body resulting from the methods of the present disclosure may include cracks near where it is connected to the substrate that can easily be removed (e.g., via a machining process, such as milling) when forming the gel body to a desired shape for a desired application; however, the gel bodies formed by the methods of the present disclosure do not have any visible cracks or voids in the portion of the gel body that will be used. In some embodiments, the gel bodies will have no visible cracks anywhere, but some cracks near the edges that can easily be removed when shaping the gel body to its desired shape are acceptable and still considered "substantially crack-free."

In some existing systems and methods for forming gel bodies, the gel bodies can crack during drying, at least in part because of the substantial shrinkage that can occur during drying, and which can be exacerbated by a larger-sized gel body. Some systems and methods have been developed to attempt to produce crack-free gel bodies of suitable sizes, but such approaches have included either expensive technological equipment or have been prohibitively and impractically time-consuming. For example, some systems and methods have included super-critical-drying of a gel body, which can be prohibitively costly. Other systems and methods have included employing drying chemical control additives (DCCAs) that help to remove water from gels without cracking, but such DCCAs can remain inside the gel body and are removed in a subsequent process during calcination of the gel. This calcinations removal process can also cause structural problems in the resulting gel (e.g., cracks, etc.). Other systems and methods have included the use of defined temperature and moisture to slowly rid the gel of water, but these approaches have been impractically time-consuming, especially as the size of the gel bodies increases and the diffusion pathways increase.

In addition, some existing systems and methods have employed sol-gel methods to form thin films (e.g., thin glass films) on a substrate, such that the resulting product includes the then formed film and the substrate.

The present inventor, however, has discovered methods for forming three-dimensional, self-supporting, monolithic gel bodies of suitably large sizes that are substantially crack-free. In some embodiments, the methods of the present disclosure include producing the gel body layer-by-layer and at least partially drying each layer of the gel body as it is produced, to at least partially avoid tensions throughout the gel body that can develop during a final drying step and which can cause cracking. That is, the methods of the present disclosure include gradually and iteratively building up a desired gel body. In the methods of the present disclosure, tension inside the gel body caused by capillary forces can be minimized, at least partially because the diffusion pathways of each individual layer are relatively short, such that each layer can be at least partially dried before application of a new layer. In some embodiments, the new layer is applied before the prior layer is completely dried or cured, which can promote a good connection or fusion between successive layers, and can facilitate the formation of a monolithic gel body.

The term "self-supporting" is generally used to refer to an object that does not collapse or deform under its own weight, and that does not require another object or substrate to maintain its desired in-use structure or shape. A self-supporting object may not necessarily be free-standing.

In some embodiments, the monolithic gel bodies of the present disclosure can be formed by a sol-gel reaction. A "sol-gel reaction" is a wet-chemical technique (sometimes also referred to as "Chemical Solution Deposition") for the fabrication of materials starting either from a chemical solution or colloidal particles (e.g. nanoscale particle) to produce an integrated network (gel). In some embodiments, sol-gel precursors can include metal alkoxides and metal chlorides, which undergo hydrolysis and polycondensation reactions to form a colloid, or sol, a system composed of solid particles (e.g., with sizes ranging from 1 nm to 1 µm) dispersed in a solvent. The sol can then evolve toward the formation of an inorganic continuous network containing a liquid phase (gel). Formation of a metal oxide can include connecting the metal centers with oxo (M-O-M) or hydroxo (M-OH-M) bridges, therefore generating metal-oxo or metal-hydroxo polymers in solution. A drying process can serve to remove the liquid phase from the gel thus forming a porous material. Afterwards, a thermal treatment (e.g., firing) may be performed in order to promote further polycondensation and densification and enhance mechanical properties.

As mentioned above, in some embodiments, the monolithic gel body resulting from the methods of the present disclosure can form, or be used to form, a dental article or appliance.

The term "dental article" is to be understood as an article which can and is to be used in the dental or orthodontic area including dental laboratories.

The term "dental appliance" generally refers to any dental or orthodontic restoration, dental mill blank, prosthetic device, or combination thereof. The appliance may be a finished appliance ready for introduction into the mouth of a patient, an appliance without the finishing (e.g. without stains) but with its final shape (i.e., a "net shape" appliance), or it may be a preformed or near-final dental appliance (i.e., a "near-net shape" appliance) subject to further processing before use, such as a dental mill blank.

The phrase "dental mill blank" generally refers to a solid block of material from which a desired product (e.g., a dental restoration) can be machined. A dental mill blank may have a size of about 10 mm to about 30 mm in two dimensions, for example may have a diameter in that range, and may be of a certain length in a third dimension. A blank for making a single crown may have a length of about 15 mm to about 30 mm, and a blank for making bridges may have a length of about 40 mm to about 80 mm. In some embodiments, a blank used for making a single crown can have a diameter of about 24 mm and a length of about 19 mm. In some embodiments, a blank used for making bridges can have a diameter of about 24 mm and a length of about 58 mm.

The term "machining" generally refers to shaping a material by a machine, and can include, but is not limited to one or more of milling, grinding, cutting, carving, or a combination thereof. In some cases, milling can be faster and more cost-effective than grinding.

The phrase "dental workpiece" generally refers to a dental appliance which has been further processed (e.g. by machining) to obtain an intentionally shaped product. A dental workpiece can be further processed (e.g. by sintering) or used as such.

The phrase "dental restoration" is generally used to refer to any restoration that can be used in the dental field, including, but not limited to, crowns, partial crowns, inlays, onlays, abutments, bridges (e.g., including 2-part, 3-part, 4-part, 5-part or 6-part bridges), implants, other suitable dental articles, and combinations thereof. The dental restoration can include a three-dimensional inner and outer surface including convex and concave structures. Compared to other ceramic articles, such as pottery or paving stones, dental restorations can be relatively small and can include filigree. The thickness of a dental restoration can vary from very thin, for example at its edges and rims (e.g., less than about 0.1 mm) to considerably thick, for example, in the biting, or occlusal, area (e.g., up to about 7 mm). In some embodiments, the thickness of a dental restoration ranges from 0.3 mm to 0.5 mm. In some embodiments, the dental restoration can comprise or consist essentially of a glass; glass ceramic; polycrystalline ceramic material, for example, comprising alumina (e.g., $Al_2O_3$), zirconia ($ZrO_2$), partly or fully stabilized zirconia (e.g., Yttrium-stabilized zirconia), titanium dioxide ($TiO_2$), high-strength oxides of the elements of the main groups II, III and IV and the subgroups III and IV, and their mixtures; metals, metal alloys, precious metals, precious metal alloys, or combinations thereof (e.g., cobalt alloys, such as cobalt-chromium, titanium alloys, gold/platinum/palladium alloys, etc., and combinations thereof); and combinations thereof. In some embodiments, the dental restoration can include at least two layers, for example, a dental core (or dental framework) and a dental veneer.

The phrase "dental core" or "dental framework" generally refers to a solid structure that can be pre-fabricated or at least partially pre-fabricated and then used as the innermost core or center layer of the layered dental appliance of the present disclosure. For example, in some embodiments, the dental core can be adapted to be coupled to or to fit over one or more of a tooth stump, an implant abutment, or the like, or combinations thereof.

The phrase "dental veneer" generally refers to a structure formed of one or more layers that can be coupled (e.g., fused) to or built upon another structure (e.g., a dental core) for color, aesthetics, texture, surface properties, etc., and, in some embodiments, to mimic the appearance of a natural tooth.

A dental core (sometimes referred to as a "dental framework") and a dental veneer can each include a three-dimensional inner and outer surface including convex and concave structures. The outer surface of the dental core can correspond to an inner surface of the dental veneer. The inner surface of the dental core can correspond to an outer surface of a prepared tooth stump, whereas the outer surface of the dental veneer can correspond to the desired (e.g., final) dental restoration.

Dental cores or frameworks can be made of or comprise at least one of a ceramic, a metal, a metal alloy, a precious metal, a precious metal alloy, and combinations thereof. Examples of ceramics can include, but are not limited to, alumina (e.g., $Al_2O_3$); zirconia ($ZrO_2$); partly or fully stabilized zirconia (e.g., Yttrium-stabilized zirconia); titanium dioxide ($TiO_2$); high-strength oxides of the elements of the main groups II, III and IV and the subgroups III and IV, and combinations thereof; and combinations thereof. Examples of metals, metal alloys, precious metals, and precious metal alloys can include, but are not limited to, cobalt alloys (e.g., cobalt-chromium), titanium alloys, gold/platinum/palladium alloys, and combinations thereof.

The term "ceramic" generally refers to an inorganic non-metallic material that can be produced by application of heat. Ceramics can be hard, porous and brittle and, in contrast to glasses or glass ceramics, can display an essentially purely crystalline structure.

A dental ceramic appliance can be classified as "pre-sintered" within the meaning of the present disclosure if the dental ceramic appliance has been treated with heat (e.g., a temperature ranging from about 500 to about 1100° C.) for about 1 to about 3 hours to such an extent that the raw breaking resistance (Weibull strength Sigma 0) of the dental ceramic appliance is within a range of about 15 to about 55 MPa or about 30 to about 50 MPa (measured according to the "punch on three ball test" (biaxial flexural strength) described in DIN EN ISO 6872, edition March 1999, with the following modifications: diameter of steel ball: 6 mm; diameter of support circle: 14 mm; diameter of flat punch: 3.6 mm; diameter of sample disc: 25 mm, thickness of sample disc: 2 mm; no grinding and polishing of samples.).

A pre-sintered dental ceramic appliance can include a porous structure and its density (e.g., which can be 3.0 g/cm$^3$ for an Yttrium stabilized $ZrO_2$ ceramic) can be less compared to a completely sintered or finally sintered (i.e., such that there will be no further sintering step) dental ceramic appliance (e.g., which can be about 6.1 g/cm$^3$ for an Yttrium stabilized $ZrO_2$ ceramic). In some embodiments, the diameter of the pores can be in a range of about 50 nm to about 150 nm (corresponding to about 500 to about 1500 Å). In some embodiments, a pore diameter can be about 120 nm.

In some embodiments, pre-sintering of a glass and/or glass ceramic material can be effected in a temperature range of about 500 to about 750° C.

The term "sintering" generally refers to making objects from a powder by heating the material (e.g., below its melting point—"solid state sintering") until its particles adhere to each other. Sintering can cause the densification of a porous material to a less porous material having a higher density. In some cases, sintering can also include changes of the material phase composition (e.g., a partial conversion of an amorphous phase toward a crystalline phase).

The terms "sintering" and "firing" are used interchangeably herein. A pre-sintered ceramic framework can shrink during a sintering step, that is, if an adequate temperature is applied. The sintering temperature to be applied depends on the ceramic material chosen. For example, for $ZrO_2$-based ceramics, a sintering temperature can range from about 1200° C. to about 1500° C. In some embodiments, $Al_2O_3$-based ceramics can be sintered at a temperature ranging from about 1300° C. to about 1700° C. In some embodiments, glass ceramic materials can be sintered at a temperature ranging from about 700 to about 1100° C. for about 1 to about 3 hours. In some embodiments, a firing step of the present disclosure can include firing at a temperature of at least about 500° C., in some embodiments, at least about 700° C., in some embodiments, at least about 1000° C., and in some embodiments, at least about 1200° C.

In some embodiments, the gel body resulting from the methods of the present disclosure can be subjected to additional drying steps to further remove moisture, and to form a porous material that may include inorganic and organic content. The porous material or the gel body can then be subjected to a calcination process, for example, to burn organic content out of the porous material or gel body to provide a substantially ceramic or inorganic body that can be used as, or further processed for use as, a dental article or appliance.

The term "calcination," and variations or derivatives thereof, can be used to refer to a process of applying heat and/or pressure, for example, to burn out organic content. In some embodiments, calcination can occur at a temperature of about 500° C.

Some methods of the present disclosure facilitate providing colored dental appliances, or precursor bodies for producing dental appliances. Coloring additives can be added early in the process (e.g. in the sol) and/or later on in the process (e.g. after formation of an individual layer of the gel body, after drying an individual layer of the gel body, after formation of the complete gel body, and/or after drying the gel body). If the coloring is to be done after a drying step, it can be done by using a coloring solution containing coloring additives (e.g. metal salts). If the coloring is to be done during formation of a layer, the coloring additives (e.g. metal salts) may already be contained in the sol.

Adding coloring additives at an early stage in the process, for example when providing the sol, can result in a homogenous distribution of the coloring additives throughout the resulting gel body, or throughout a layer of the resulting gel body.

FIG. 1 illustrates a flowchart of a method 100 for forming a gel body, according to one embodiment of the present disclosure. As shown in FIG. 1, the method 100 can include providing a substrate 102, a sol 104, and an ammonia atmosphere 106.

As will be described in greater detail below, a variety of substrate shapes and surface features or textures can be employed. In some embodiments, the substrate 102 can include a substantially rod-like or cylindrical shape. In some embodiments, the substrate 102 can include at least a portion having a conical or frusto-conical shape. In some embodiments, the substrate 102 can be shaped and dimensioned so as to penetrate at least a portion of the resulting gel body, and in some embodiments, the substrate 102 can be shaped and dimensioned to include a surface, from which the gel body can extend.

Furthermore, the substrate 102 can be formed of a variety of materials suitable for supporting a gel body during the method 100. Examples of substrate materials that can be used can include, but are not limited to, organic polymers (e.g., PTFE, PMMA, PP, PE, etc.), metals (e.g. steel), metal oxides (e.g. alumina), or combinations thereof.

The sol 104 can include a variety of colloidal suspensions including various metal salts of interest. Examples of suitable sols of the present disclosure can include, but are not limited to, zirconia sols (e.g., acetate-stabilized zirconia sols, nitrate-stabilized zirconia sols, etc., or combinations thereof), acid-stabilized alumina sols, silica sols, or combinations thereof.

For example, in some embodiments, the sol 104 can include zirconia, and the zirconia sol can be stabilized by an acid or base, e.g. acetic acid. For example, in some embodiments, the sol can include zirconium acetate (or an "acetate-stabilized zirconia sol") that includes excess acetic acid to stabilize the zirconia sol.

The sol 104, particularly, a zirconia sol 104, can be cured to form a gel by exposing the sol 104 to the ammonia atmosphere 156. For example, in embodiments employing an acetate-stabilized zirconia sol, ammonia can cause the sol 104 cure and harden, which can form ammonium acetate throughout the gel body. This volatile salt of ammonium acetate can later be burned out of the dried gel body (e.g., via a calcination process) to produce a porous zirconia body. Other methods can also be used to remove the ammonium acetate from the dried gel body.

The ammonia atmosphere 156 can be provided by a variety of means, including providing a sufficient amount and/or concentration of an ammonia solution that will provide a sufficient amount of ammonia vapor above its liquid surface. A sufficient amount and/or concentration of the ammonia solution and vapor can be an amount that is necessary to cure a desired amount of the sol 104 to form a gel. In some embodiments, the amount and/or concentration of the ammonia solution can be adjusted to control the time required to dry or cure each layer of the sol 104 that is applied to the substrate 102. The ammonia atmosphere 106 need not necessarily be contained or completely pure, but rather, in some embodiments, can be open to ambience.

With continued reference to FIG. 1, the method 100 can further include applying a first quantity of the sol 104 to the substrate 102 to form a first coated substrate 108 comprising a first layer (or coating) of the sol 104 on the substrate 102. The first quantity of the sol 104 should be of a sufficient viscosity and amount to form the first layer to a desired size and thickness. That is, in some embodiments, the viscosity of the sol 104 can control the thickness of the layers applied to the substrate 102. Various techniques can be employed to control the amount and thickness of the sol that is deposited onto the substrate 102, which is described in greater detail below.

The first coated substrate 108 can then be exposed to, or positioned in, the ammonia atmosphere 106 to cure the first layer of the sol 104 to form a first supported gel 110 comprising the substrate 102 and the first gel layer supported on the substrate 102.

Any drying or curing step of the present disclosure can be characterized by at least one of the following features:
 duration: up to about 2 hours, or up to about 10 minutes, or up to about 1 minute;
 temperature: from about 0 to about 120° C., or about 20 to about 100° C., in some embodiments, room temperature (e.g., 25° C.); and/or
 pressure: ambient pressure.

In some embodiments, the drying/curing step of each layer formed on the substrate 102 include allowing the network-formation of the gel to begin without completely drying the gel. As mentioned above, in such embodiments, a second quantity of the sol 104 can be applied to the first supported gel 110 prior to completely drying the first gel layer, such that the second quantity of the sol 104 can adhere or connect well with the first layer.

Drying can be performed at ambient conditions (e.g., room temperature (e.g., 25° C.) and atmospheric pressure (e.g., 1 atm)) by simply holding the first coated substrate 108 in the ammonia atmosphere 106 for a sufficient period of time and/or by holding the first coated substrate 108 open to the air after curing with ammonia vapor.

As shown in FIG. 1, the method 100 can further include applying a second quantity of the sol 104 to the first supported gel 110 to form a second coated substrate 112 comprising a second layer (or coating) formed on the first supported gel 110. The second coated substrate 112 can then be exposed to, or positioned in, the ammonia atmosphere 106 to cure the second layer of the sol 104 to form a second supported gel 114 comprising the second gel layer and the first gel layer supported on the substrate 102. The second gel layer and the first gel layer can morph together as one, such that the second support gel 114 includes a monolithic gel body (i.e., without any distinction between the first and second layers) supported on the substrate 102.

In some embodiments, the method 100 can include at least two layering steps. For example, in some embodiments, the method 100 can include tens of layering steps, in some embodiments, hundreds of layering steps, and in some embodiments, even more. In each embodiment, however, the method 100 can form a monolithic gel body supported on the substrate 102 that includes no visible distinction between the layers used to form the monolithic body.

In some embodiments, the method 100 includes only the two layering steps described above, such that the second gel layer forms the outermost surface of the resulting gel body. In such embodiments, the second curing step in which the second coated substrate 112 is exposed to the ammonia atmosphere 106 can be a final curing step, in which the second layer can be cured, and the entire gel (including the first layer) can be further hardened or cured. For example, in some embodiments, the second coated substrate 112 can be held in the ammonia atmosphere 106 for a longer period of time than the first coated substrate 108 was held in the ammonia atmosphere 106. By way of further example, in some embodiments, the second coated substrate 112 can be exposed to a more highly concentrated ammonia atmosphere 106 than the first coated substrate 108.

In some embodiments, the method 100 can continue (as represented in FIG. 1 by the ellipsis), and can include as many layering steps (i.e., applying the sol 104, using the ammonia atmosphere 106 to cure the sol to form a gel, etc.) as necessary to form a gel body having the desired size characteristics. When the desired gel has been obtained, the gel can be supported on the substrate 102, and can be additionally cured or dried on the substrate 102, or the gel can be removed from the substrate 102 and additionally cured or dried. In some embodiments, the supported gel (i.e., supported on the substrate 102) can be stored for future use.

Eventually, as shown in FIG. 1, to form the desired self-supporting monolithic gel body, the method 100 can include removing the substrate 102 from the resulting gel body to form a self-supporting monolithic gel body 120. The monolithic gel body can be referred to as a "gel body" in its wet or dry state, and in some embodiments, until it is sintered.

The second supported gel 114 (or the "final" supported gel, if the method 100 includes more than two layering steps) and/or the self-supporting monolithic gel body 120 can be further dried, cured, calcined, machined, fired, or the like, as determined by the final application of the gel body.

In some embodiments, one or more of the substrate 102, the sol 104, the ammonia atmosphere 106, and any other tools necessary to perform the steps of the method 100 can form a system 150 of the present disclosure for making the self-supporting monolithic gel body 120.

As mentioned above, in some embodiments, the resulting self-supporting gel body 120 can be used in, or further processed for use in, various dental applications. In addition, in some embodiments, the self-supporting gel body 120 may have applications in various optics fields, for example, as a lens, due at least in part to its monolithic (and in some embodiments, transparent) property. Due at least in part to its large inner surface (e.g., as a result of where the substrate 102 may have extended into the gel body), the gel can also be used as a catalyst or a catalyst support.

As will be described in greater detail below with reference to FIGS. 2 and 3, applying the sol 104 (e.g., in the first, second, or subsequent layering steps) can be accomplished in a variety of ways, including, but not limited to, dipping, decanting (e.g., with a nozzle, a syringe, a spout, a pipette, etc.), applying droplets (e.g., with a nozzle, a syringe, a spout, a pipette, etc.), or a combination thereof. In addition, any of these application methods can further include rotating the substrate while applying the sol 104.

While the same sol 104 and ammonia atmosphere 106 are shown as being used in the method 100 (e.g., a first quantity of the sol 104, a second quantity of the sol 104, etc.), it should be understood that a new sol 104 and/or ammonia atmosphere 106 can instead be used in each subsequent layering step. In such embodiments, the second sol formulation can be the same as or different from the first sol formulation. Similarly, the second ammonia atmosphere can be the same as or different from the first ammonia atmosphere (e.g., as mentioned above, one ammonia atmosphere can be more highly concentrated than another).

As evident from the above description, the method 100 does not include any molds, dies, or other shaping tools for forming the gel, or the individual layers of the gel. In some embodiments, the shape, structure and/or surface features of the substrate 102 can control the shape and size of the resulting gel; however, gels formed according to methods of the present disclosure may not have a very precise or prescribed shape or size, but rather can include a variety of shapes (including irregular shapes) that can be further manipulated or developed in downstream processes.

One potential advantage in forming the gel without the use of any molds, dies or other shaping tool is that any problems associated with removal of the gel from the molds or dies can be avoided.

The method 100 can be performed manually, for example, for a small-scale production, or the method 100 can be automated or semi-automated, for example, for a larger-scale production.

Figure 2:
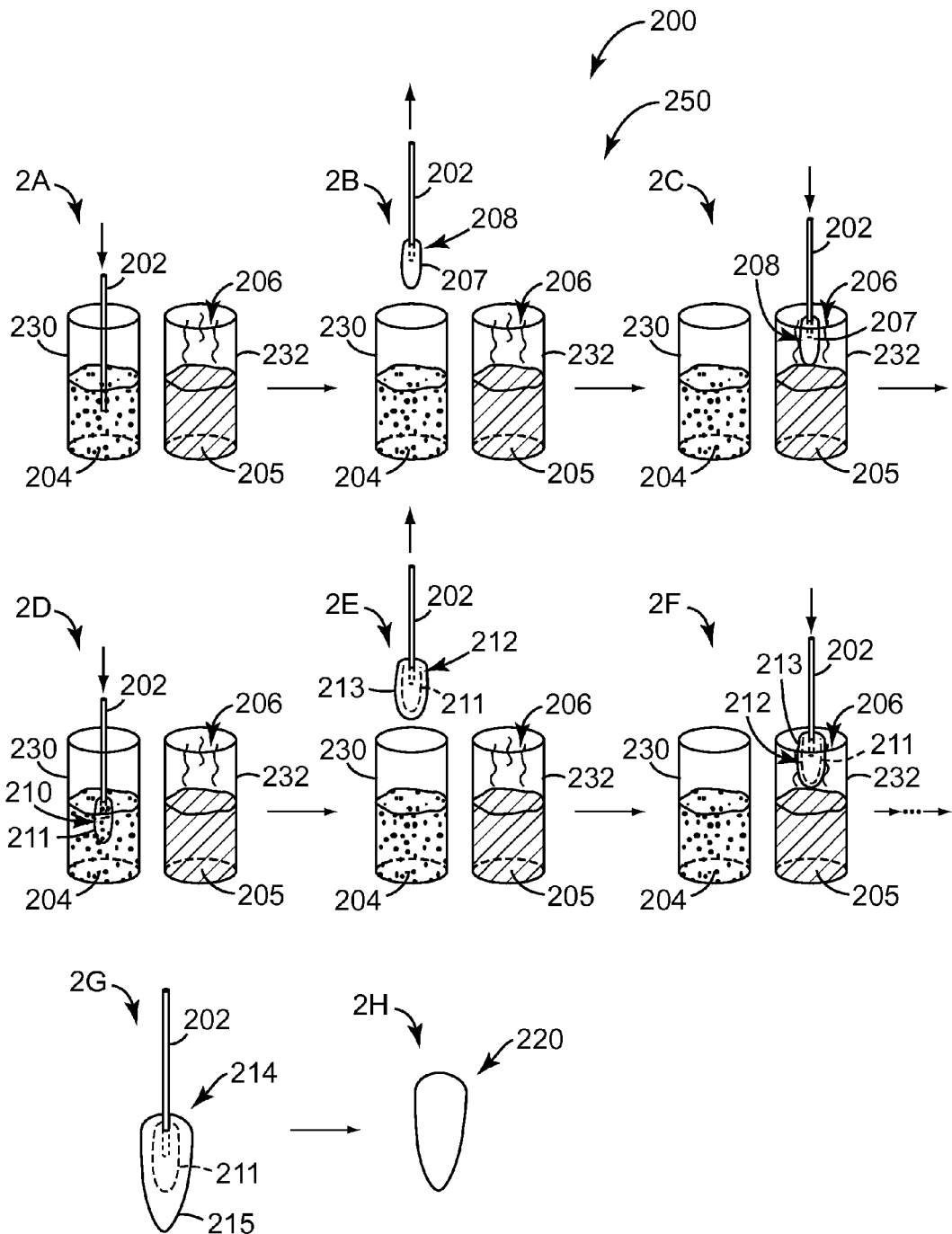
FIG. 2 is a schematic flowchart illustrating a method according to another embodiment of the present disclosure and schematically illustrates a system according to another embodiment of the present disclosure.

FIG. 2 illustrates a schematic flowchart of a method 200 according to one embodiment of the present disclosure and a schematic representation of a system 250 according to one embodiment of the present disclosure. The method 200 and the system 250 share many of the same elements and features described above with reference to the illustrated embodiment of FIG. 1. Accordingly, elements and features corresponding to elements and features in the illustrated embodiment of FIG. 1 are provided with the same reference numerals in the 200 series. Reference is made to the description above accompanying FIG. 1 for a more complete description of the features, elements or method steps (and alternatives to such features, elements and steps) of the embodiment illustrated in FIG. 2.

The illustrated method 200 includes steps 2A-2H, and the illustrated system 250 includes a substrate 202, a sol 204, an ammonia solution 205, an ammonia atmosphere 206, a first container (or sol source) 230 adapted to contain the sol 204, and a second container 232 adapted to contain the ammonia solution 205 and at least a portion of the ammonia atmosphere 206.

As FIG. 2 is a schematic representation of the method 200 and the system 250, it should be understood that the shapes, sizes and relative shapes and sizes of the various features and elements are shown for illustration purposes only.

Steps 2A-2C of the method 200 generally produce a first layer of the gel body, and steps 2D-2F generally produce a second layer. Steps 2D-2F can be repeated to produce a gel body on the substrate 202 having the desired size and characteristics.

As shown in FIG. 2, in a first step 2A of the method 200, the substrate 202 can be positioned in the first container 230 and dipped into the sol 204 to apply a first quantity of sol 204 to the substrate 202. As shown in FIG. 2, in a second step 2B of the method 200, the substrate 202 can be removed from the sol 204, forming a first coated substrate 208 comprising a first layer or coating 207 formed on at least a portion of the substrate 202, such as a distal end or bottom portion of the substrate 202.

The rate at which the substrate 202 is dipped into the sol 204 in each layering step of the method 200 can be controlled to control the thickness of each layer that is applied. For example, at least partially due to the physical properties of the sol 204, in some embodiments, a slower dipping rate (e.g., including the rate the substrate 202 is pulled out of the sol 204) can result in a thinner layer of sol 204 being formed on the substrate 202. Conversely, in some embodiments, a faster dipping rate can result in a thicker layer of sol 204 being formed on the substrate 202.

In addition, in some embodiments, the viscosity of the sol 204 can affect the thickness of each layer that is applied onto the substrate 202. For example, a more viscous sol 204 can result in a thicker layer being formed, and a less viscous sol 204 can result in a thinner layer being formed.

In some embodiments, each wet sol layer or coating formed during any of the methods of the present disclosure can be no greater than about 500 micrometers thick (0.5 mm), in some embodiments, no greater than about 200 micrometers thick (0.2 mm), and in some embodiments, no greater than bout 100 micrometers thick (0.1 mm).

As further shown in FIG. 2, in a third step 2C of the method 200, the first coated substrate 208 can then be positioned in the ammonia atmosphere 206 created by the ammonia solution 205, for example, by positioning at least the coated portion at least partially into the second container 232, as shown, or by holding the first coated substrate 208 over the container 232 in such a way that the first coated substrate 208 is contacted with a sufficient amount of the ammonia atmosphere 206 to at least partially cure the sol 204 of the first layer 207. Exposing the first coated substrate 208 to the ammonia atmosphere 206 can then at least partially cure the first layer 207 to form a first supported gel 210 comprising a first gel layer 211 coupled to, or supported by, the substrate 202, which is shown in step 2D.

With continued reference to FIG. 2, the method 200 can further include a fourth step 2D in which a second quantity of the sol 204 can be applied to the first supported gel 210. For example, as shown, at least a portion of the first supported gel 210 can be dipped into the sol 204 to apply a second quantity of the sol 204 to the first gel layer 211 of the first supported gel 210. In a fifth step 2E of the method 200, the substrate can again be removed from the sol 204, forming a second coated substrate 212 comprising a second layer or coating 213 formed on the first supported gel 210, such that the second coated substrate 212 comprises the substrate 202, the second layer 213 and the first gel layer 211 positioned intermediately of the substrate 202 and the second layer 213.

In a sixth step 2F of the method 200, at least a portion of the second coated substrate 212 can then be positioned in the ammonia atmosphere 206 in the same possible ways as described above with respect to the first coated substrate 208 to contact the second coated substrate 212 with the ammonia atmosphere 206 to at least partially cure the sol 204 of the second layer 213 and/or further cure the sol 204 of the first layer 207. Exposing the second coated substrate 212 to the ammonia atmosphere 206 can at least partially cure the second layer 213 to form a second supported gel 214, and can additionally further cure the first gel layer 211. An example of the second supported gel 214 is shown in step 2G of the method 200. As shown, the second supported gel 214 can include a second gel layer 215 and the first gel layer 211 coupled to, or supported by, the substrate 202.

As a result, as illustrated by the method 200 shown in FIG. 2, the substrate 202 can be moved iteratively from the sol 204 to form a layer or coating, to the ammonia atmosphere 206 to cure the layer, and back to the sol 204 for another layer, and so on, which is represented by the ellipsis in the method 200. Particularly, the substrate 202 is illustrated in FIG. 2 as being iteratively dipped into the sol 204 and then dipped down into the ammonia atmosphere 206. In some embodiments, the substrate 202 can be rotated, for example, about its longitudinal axis that runs parallel to its length. Such a rotation can promote symmetry in the resulting gel body.

The first gel layer 211 is shown in step 2G for illustrations purposes only. However, even though the method 200 includes an iterative layering process, it should be understood that the systems and methods of the present disclosure can produce monolithic bodies, such that the layers making up the gel body are not visible, or visibly distinguishable, in the resulting gel body.

As shown in step 2H of FIG. 2, the method 200 can further include removing the substrate 202 form the supported gel 214 (or vice versa) to form a monolithic gel body 220 that can be further dried, cured, calcined, machined and/or fired. Unlike some existing systems and methods for forming thin glass films, the gel body 220 includes a three-dimensional shape and is self-supporting, and the substrate 202 does not form a portion of the gel body 220. Various features and dimensions of the resulting gel body are described in greater detail below, along with comparisons (e.g., dimensional ratios) of the resulting gel body and the substrate 202.

In some embodiments, prior to removing the substrate 202, the supported gel 214 can be subjected to the ammonia atmosphere 206 again for further hardening or curing of the various layers making up the gel 214.

In some embodiments of the method 200, a new sol 204 and/or ammonia atmosphere 206 can be provided for each layering step (e.g., for each sequence of 2D-2F). As a result, in some embodiments, the system 250 can include a plurality of first containers 230, a plurality of second containers 232, a plurality of sols 204, a plurality of ammonia solutions 205, and/or a plurality of ammonia atmospheres 206. In embodiments employing multiple containers 230, sols 204, ammonia solutions 205, and/or ammonia atmospheres 206, the multiple containers 230, sols 204, ammonia solutions 205, and/or ammonia atmospheres 206 can all be the same or different, as explained above with respect to the method 100 illustrated in FIG. 1. In addition, multiple substrates 202 can be used at once according to the method 200 of FIG. 2. In such embodiments, the multiple substrates 202 can be dipped in the same first container 230 and held in the same second container 232, or each of the substrates 202 can be dipped in its own set of containers 230, 232, or a combination thereof.

Figure 3:
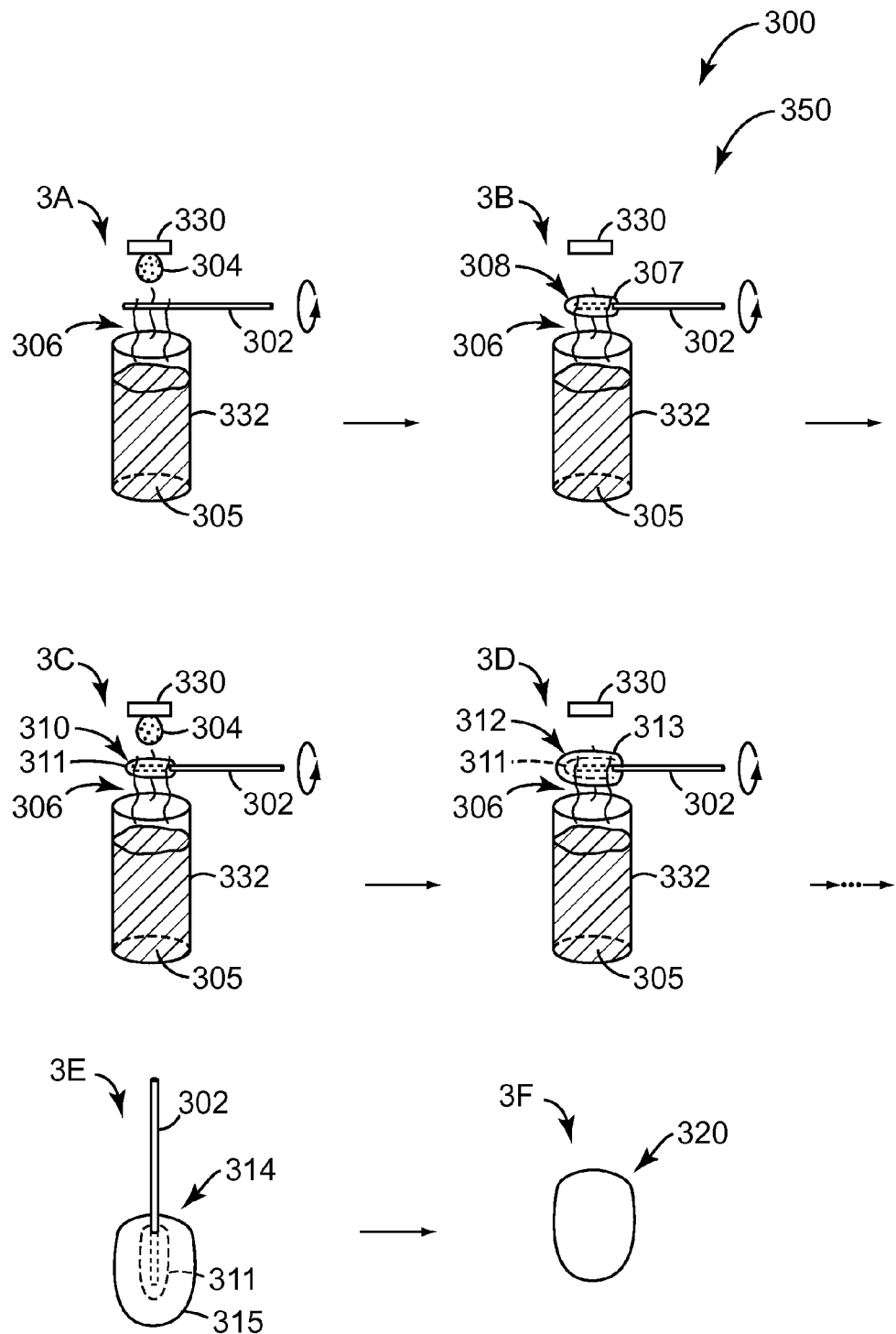
FIG. 3 is a schematic flowchart illustrating a method according to another embodiment of the present disclosure and schematically illustrates a system according to another embodiment of the present disclosure.

FIG. 3 illustrates a schematic flowchart of a method 300 according to another embodiment of the present disclosure and a schematic representation of a system 350 according to another embodiment of the present disclosure. The method 300 and the system 350 share many of the same elements and features described above with reference to the illustrated embodiments of FIGS. 1 and 2. Accordingly, elements and features corresponding to elements and features in the illustrated embodiment of FIGS. 1 and 2 are provided with the same reference numerals in the 300 series. Reference is made to the description above accompanying FIGS. 1 and 2 for a more complete description of the features, elements or method steps (and alternatives to such features, elements and steps) of the embodiment illustrated in FIG. 3.

The illustrated method 300 includes steps 3A-3F, and the illustrated system 350 includes a substrate 302, a sol 304, an ammonia solution 305, an ammonia atmosphere 306, a sol source 330, and a container 332 adapted to contain the ammonia solution 305 and at least a portion of the ammonia atmosphere 306.

As FIG. 3 is a schematic representation of the method 300 and the system 350, it should be understood that the shapes, sizes and relative shapes and sizes of the various features and elements are shown for illustration purposes only.

In the method 300, the sol 304 can be applied onto the substrate 302, and the substrate 302 can then be rotated about its longitudinal axis to distribute the sol 304 over the rod-like substrate 302. Meanwhile, at least the portion of the substrate 302 onto which the sol 304 is being applied can be positioned in the ammonia atmosphere 306 to cure the sol 304 to form a gel. The substrate 302 can be rotated continuously or intermittently, and the rotation of the substrate 302 can begin prior to application of the sol 304 and can continue while the substrate 302 is positioned in the ammonia atmosphere 306, or the rotation can be paused intermittently.

The sol 304 can be provided by the sol source 330, which can include a nozzle, a spout (e.g., of a container from which the sol 304 can be decanted or poured), a syringe, a pipette, or a combination thereof. That is, the sol 304 can be applied at least one of decanting, pipetting, or the like, or combinations thereof. In some embodiments, the sol 304 can be applied in a dropwise fashion, such that a bolus or droplet of sol 304 is deposited onto the substrate 302 at a time. That is, in some embodiments, the sol 304 can be applied to the substrate 302 continuously or intermittently, for example, while the substrate 302 is turned.

By way of example only, in some embodiments, in a first step 3A of the method 300, the substrate 302 can be positioned over the container 332 such that at least a portion of the substrate 302 is exposed to a sufficient amount and/or concentration of ammonia from the ammonia atmosphere 306. A first quantity of sol 304 can be applied to the substrate 302, and the substrate 302 can be rotated, forming a first coated substrate 308 (see step 3B) comprising a first layer or coating 307 formed on at least a portion of the substrate 302, such as a distal end of the substrate 302.

The amount or size of the quantity (e.g., droplet size) of the sol 304 that is applied at each step of the method 300 can affect the thickness of the each layer that is formed. In some embodiments, the thickness of successive layers can be approximately the same or can increase or decrease. In addition, in embodiments in which the substrate 302 is rotated either while or just after the sol 304 is applied, the rate of rotation of the substrate 302 can affect the homogeneous distribution of each layer that is formed. For example, a faster rotation rate can spread the sol 304 out more quickly, leading to a homogeneous layer, while a slower rotation rate can lead to an asymmetric layer.

As shown in a second step 3B of the method 300, the first coated substrate 308 can remain positioned in the ammonia atmosphere 306 (or temporarily removed and then repositioned in the ammonia atmosphere 306) in such a way that the first coated substrate 308 is contacted with a sufficient amount of the ammonia atmosphere 306 to at least partially cure the sol 304 of the first layer 307. Exposing the first coated substrate 308 to the ammonia atmosphere 306 can at least partially cure the first layer 307 to form a first supported gel 310 comprising a first gel layer 311 coupled to, or supported by, the substrate 302, which is shown in step 3C.

With continued reference to FIG. 3, the method 300 can further include a third step 3C in which a second quantity of the sol 304 can be applied to the first supported gel 310. For example, as shown, a second quantity of the sol 304 can be dispensed from the sol source 330 and applied onto the outer surface of at least a portion of the first supported gel 310, and the substrate 302 can be rotated, forming a second coated substrate 312 (see step 3D). The second coated substrate 312 can include a second layer or coating 313 formed on the first supported gel 310, such that the second coated substrate 312 comprises the substrate 302, the second layer 313 and the first gel layer 311 positioned intermediately of the substrate 302 and the second layer 313.

As shown in a fourth step 3D of the method 300, the second coated substrate 312 can remain positioned in the ammonia atmosphere 306 (or temporarily removed and then repositioned in the ammonia atmosphere 306) in such a way that the second coated substrate 312 is contacted with a sufficient amount of the ammonia atmosphere 306 to at least partially cure the sol 304 of the second layer 313. Exposing the second coated substrate 312 to the ammonia atmosphere 306 can at least partially cure the second layer 313 to form a second supported gel 314, and can additionally further cure the first gel layer 311. An example of the second supported gel 314 is shown in step 3E of the method 300. As shown, the second supported gel 314 can include a second gel layer 315 and the first gel layer 211 coupled to, or supported by, the substrate 302.

Again, the first gel layer 311 is shown in step 3E for illustrations purposes only, and it should be understood that the systems and methods of the present disclosure can produce monolithic bodies, such that the layers making up the gel body are not visible, or visibly distinguishable, in the resulting gel body.

As shown in step 3F of FIG. 3, the method 300 can further include removing the substrate 302 form the supported gel 314 (or vice versa) to form a monolithic gel body 320 that can be further dried, cured, calcined, machined and/or fired. Unlike some existing systems and methods for forming thin glass films, the gel body 320 includes a three-dimensional shape and is self-supporting, and the substrate 302 does not form a portion of the gel body 320.

The method 300 described above and shown in FIG. 3 is represented as a discrete step-wise method by way of example only and for the sake of clarity. However, it should be understood that in some embodiments, the method 300 can be more continuous than what is depicted in FIG. 3. That is, in some embodiments, as shown in FIG. 3, a first quantity of the sol 304 can be applied to the substrate 302 to form a layer or coating, the layer can be cured to form a gel by being held in the ammonia atmosphere, and then a second quantity of the sol 304 can be applied, and so on. Alternatively, in some embodiments, the sol 304 can be dispensed or applied onto the substrate 302 substantially continuously, while at least a portion of the substrate 302 is maintained in the ammonia atmosphere 306, and optionally rotated, such that the gel body can be built up gradually. In some embodiments, the rotation can be timed such that one layer is equivalent to about one revolution of the substrate 302, but in some embodiments, the application of the sol 304 is continuous to the point where it may not be immediately clear where one layer begins and another layer ends, but an iterative layering process is used to build up a coating on the substrate 302 that is cured as it is built up, to facilitate forming a substantially crack-free supported gel 314, and ultimately, self-supporting gel body 320.

As described above, in some embodiments, prior to removing the substrate 302, the supported gel 314 can be subjected to the ammonia atmosphere 306 again for further hardening or curing of the various layers making up the gel 314.

The methods 200 and 300 of FIGS. 2 and 3 are shown and described as separate methods by way of example only. However, it should be understood that in some embodiments, the method of producing a gel body according to the present disclosure can include any combination of the steps of the methods 200 and 300. For example, in some embodiments, a first gel layer can be formed on the substrate by dipping and then exposing to an ammonia atmosphere, and then subsequent layers can be formed by holding the substrate in an ammonia atmosphere while applying additional sol onto the first gel layer, and so on. Other combinations of the methods 200 and 300 can be envisioned, given the teachings of the present disclosure.

Figure 4A:
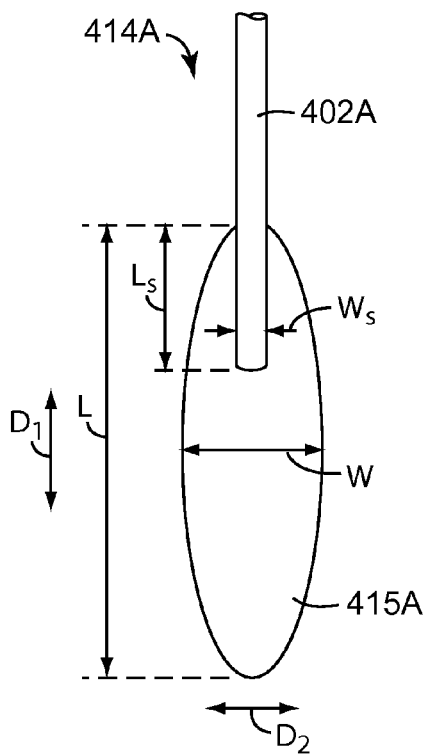
FIGS. 4A-4C are schematic cross-sectional views of exemplary gel bodies produced according to the methods of the present disclosure, supported by various substrates of the present disclosure.
Figure 4B:
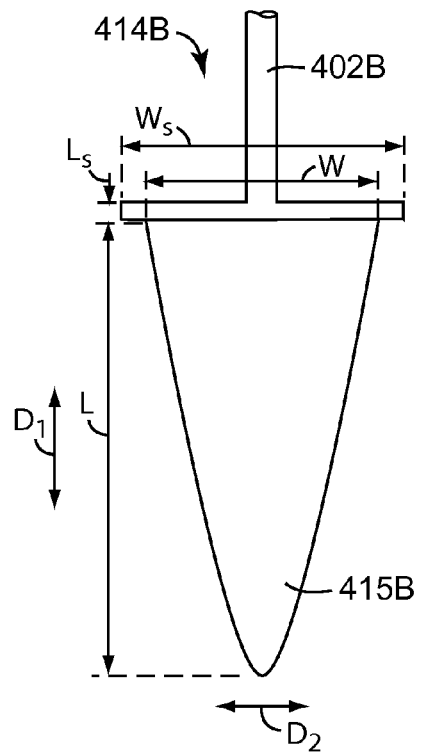
Figure 4C:
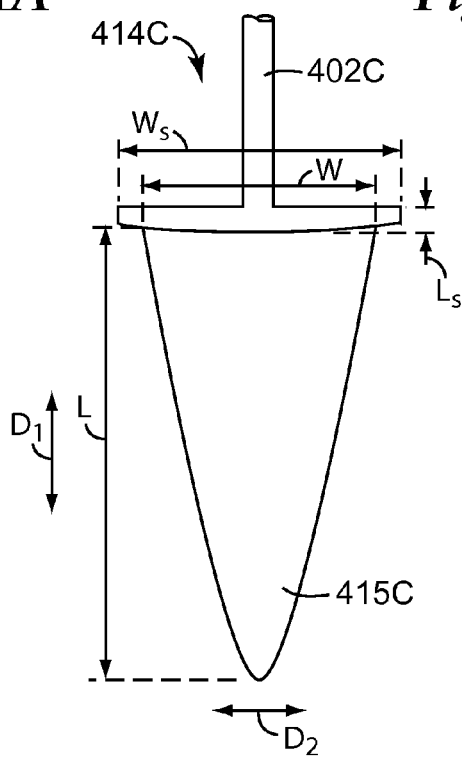

FIGS. 4A-4C illustrate exemplary supported gels 414A, 414B and 414C that can be formed according to methods of the present disclosure. By way of example only, the supported gel 414A shown in FIG. 4A includes a gel body 415A supported on a rod-like substrate 402A, and could be the result of either of the methods 200 and 300 shown in FIGS. 2 and 3 and described above.

Each of the supported gels 414A, 414B and 414C includes a gel body 415A, 415B, 415C coupled to a substrate 402A, 402B, 402C, respectively, and the substrate 402A, 402B, 402C can be removed to form a self-supporting gel body.

As shown in FIGS. 4A-4C in some embodiments, the gel body 415A, 415B, 415C resulting from the methods of the present disclosure, while still in an at least partially wet state, can include a maximum length L in a first direction $D_1$. For example, in the supported gel 414A, the first direction $D_1$ can extend substantially along the length of the rod-like substrate 402A. As further shown in FIGS. 4A-4C, the gel body 415A, 415B, 415C can include a maximum width W in a second direction $D_2$ that is oriented substantially perpendicularly to the first direction $D_1$ and the length L. In embodiments in which a substantially round or conical gel body 415A, 415B, 415C is formed, the "width W" may actually be the diameter of the gel body 415A, 415B, 415C. Thus, the term "width" is used by way of example only and is only meant to represent a transverse dimension in the second direction $D_2$.

Gel bodies formed according to methods of the present disclosure can take on a variety of three-dimensional shapes. As exemplified in FIGS. 4A-4C, the resulting shape of the gel body 415A, 415B, 415C can depend at least in part on the shape and structure of the substrate 402A, 402B, 402C that is used in the process, and can also depend on the method(s) used to form the gel body 415A, 415B, 415C. For example, the gel body 415A can be the result of either the method 200 shown in FIG. 2 or the method 300 shown in FIG. 3. The substrates 402B and 402C, however, would more likely be used according to the dipping method 200 shown in FIG. 2 or a combination of the methods 200 and 300 shown in FIGS. 2 and 3.

The following exemplary dimensions and properties of the gel bodies 415A, 415B, 415C are provided assuming the gel bodies are at least partially wet gel bodies.

In some embodiments, the length L can be at least about 1 cm, in some embodiments at least about 2 cm, and in some embodiments, at least about 3 cm. In some embodiments, the length L can be no greater than about 5 cm, and in some embodiments, no greater than about 4 cm, depending on the size of the substrate 402A, 402B, 402C.

In some embodiments, the width W can be at least about 0.25 cm, in some embodiments, at least about 0.5 cm, and in some embodiments, at least about 1 cm. In some embodiments, the width W can be no greater than about 3 cm, in some embodiments, no greater than about 2 cm, and in some embodiments, no greater than about 1.5 cm. In some embodiments, the width W can be about 1.8 cm, depending on the size of the substrate 402A, 402B, 402C.

In some embodiments, the maximum size and weight of the gel body 415A, 415B, 415C can be at least partially determined by the ratio of the weight of the gel body 415A, 415B, 415C to the total interfacial area between the substrate 402A, 402B, 402C and the gel body 415A, 415B, 415C. For example, in the embodiment illustrated in FIG. 4A, the interfacial area can be about 30 mm$^2$. This area can be increased or decreased, for example, by allowing the substrate 402A to extend a greater distance into or a lesser distance into the gel body 415A, respectively. In other embodiments, such as in the embodiments shown in FIGS. 4B and 4C, the interfacial area can be about 250 mm$^2$. As a result, depending on substrate configuration, the interfacial area can be at least about 10 mm$^2$, in some embodiments, at least about 50 mm$^2$, and in some embodiments, at least about 100 mm$^2$. In some embodiments, the interfacial area can be no greater than about 10,000 mm$^2$, in some embodiments, no greater than about 2,500 mm$^2$, and in some embodiments, no greater than about 1,000 mm$^2$.

In some embodiments, depending on the size of the substrate 402A, 402B, 402C, the mass of the resulting wet gel body 415A, 415B, 415C alone (i.e., not including the substrate 402A, 402B, 402C) can be at least about 1 g, in some embodiments, at least about 2 g, and in some embodiments, at least about 3 g. In some embodiments, the mass of the resulting wet gel body 415A, 415B, 415C alone can be no greater than about 4 g, no greater than about 3.6 g. If larger substrates 402A, 402B, 402C are used, gels having greater masses can be produced.

In some embodiments, the ratio of the mass of the wet gel body 415A, 415B, 415C to the interfacial area can affect how large the gel body 415A, 415B, 415C will be allowed to get before its own weight causes it to fall off of the substrate 402A, 402B, 402C, essentially stopping the process of making the gel. In some embodiments employing a rod-like substrate 402A, as shown in FIG. 4A, the ratio of the mass of the gel body to the interfacial area between the gel body and the substrate can be no greater than about 0.15 g/mm$^2$, in some embodiments, no greater than about 0.12 g/mm$^2$, and in some embodiments, no greater than about 0.1 g/mm$^2$.

In some embodiments employing a flat (e.g., plate-like or disc-like) substrate, such as the substrates 402B and 402C shown in FIGS. 4B and 4C, the interfacial area might be larger, allowing for the production of heavier gel bodies 415B and 415C, according to the determined ratio of the weight of the gel body to the interfacial area between the gel body and the substrate.

In some embodiments, the adhesion between the gel body 415A, 415B, 415C and the interfacial area of the substrate 402A, 402B, 402C can be increased by increasing the size of the substrate 402A, 402B, 402C (and accordingly, increasing the interfacial area) and/or by changing the surface properties in at least a portion of the interfacial area. For example, in some embodiments, the material forming the interfacial area can be changed and/or the surface roughness of at least a portion of interfacial area can be increased in order to increase the ability to form a larger gel before the gel body 415A, 415B, 415C falls off of the substrate 402A, 402B, 402C. Namely, the ratio of the weight of the gel body to the interfacial area between the gel body and the substrate can be increased. However, such changes to the interfacial area may make it more difficult to cleanly remove the gel body 415A, 415B, 415C from the substrate 402A, 402B, 402C when desired.

In some embodiments, the density of an at least partially wet resulting gel body 415A, 415B, 415C alone (i.e., not including the substrate 402A, 402B, 402C), e.g., formed from an acetate-stabilized zirconia sol, can be at least about 1.2 g/cm$^3$, in some embodiments, at least about 1.5 g/cm$^3$, and in some embodiments, at least about 1.7 g/cm$^3$. In its completely dry state, in some embodiments, the density of the gel body 415A, 415B, 415C can be at least about 2 g/cm$^3$, in some embodiments, at least about 2.4 g/cm$^3$, and in some embodiments, at least about 3.2 g/cm$^3$.

In some embodiments, as shown in FIG. 4B, the substrate 402B does not extend into the length of the gel body 415B at all. However, in some embodiments, as shown in FIGS. 4A and 4C, the substrate 402A, 402C can extend into the gel body 415A, 415C. Whether the substrate 402A, 402B, 402C includes a portion that extends into the gel body 415A, 415B, 415C, the portion of the substrate 402A, 402B, 402C to which the gel body 415A, 415B, 415C is coupled can include a maximum length $L_S$ that extends in the first direction $D_1$. In some embodiments, the ratio of the length $L_S$ of the substrate 402A, 402B, 402C to the length L of the gel body 415A, 415B, 415C can be at least about 0 (e.g., if a very thin plate-like substrate 402B is employed), in some embodiments, at least about 0.05, in some embodiments, at least about 0.1, and in some embodiments, at least 0.33. In some embodiments, the ratio of the length $L_S$ to the length L can be no greater than 1.2, in some embodiments, no greater than 0.7, and in some embodiments, no greater than 0.5. In some embodiments, the ratio of the length $L_S$ to the length L can range from about 0.01 to about 1, and in some embodiments, from about 0.1 to about 0.5.

In addition, in some embodiments, the portion of the substrate 402A, 402B, 402C to which the gel body 415A, 415B, 415C is coupled can include a maximum width $W_S$ that extends along the second direction $D_2$. In some embodiments, the ratio of the width $W_S$ of the substrate 402A, 402B, 402C to the width W of the gel body 415A, 415B, 415C can be at least about 0.01, in some embodiments, at least about 0.1, and in some embodiments, at least about 0.2. In some embodiments, the ratio of the width $W_S$ to the width W can be no greater than about 1.5, (e.g., if a plate-like substrate 402B, 402C is employed), in some embodiments, no greater than about 1, in some embodiments, no greater than about 0.75, in some embodiments, no greater than about 0.5, and in some embodiments, no greater than bout 0.25. In some embodiments, the ratio of the width $W_S$ to the width W can range from about 0.01 to about 1.

EMBODIMENTS

Embodiment 1 is a method for making a monolithic gel body, the method comprising:
  providing a substrate;
  providing a sol;
  providing an ammonia atmosphere;
  applying a first quantity of the sol to the substrate to form a first coated substrate;
  positioning the first coated substrate in the ammonia atmosphere to cure the first quantity of sol to form a first supported gel comprising a first gel supported by the substrate; and
  applying a second quantity of the sol to the first supported gel to form a second coated substrate comprising the second quantity of sol and the first supported gel.

Embodiment 2 is the method of embodiment 1, wherein at least one of applying a first quantity of the sol and applying a second quantity of the sol includes decanting the sol.

Embodiment 3 is the method of embodiment 2, wherein decanting the sol includes decanting the sol dropwise.

Embodiment 4 is the method of embodiment 1, wherein at least one of applying a first quantity of the sol and applying a second quantity of the sol includes dipping the substrate into the sol.

Embodiment 5 is the method of any of embodiments 1-4, wherein at least one of applying a first quantity of the sol and applying a second quantity of the sol occurs while rotating the substrate.

Embodiment 6 is the method of any of embodiments 1-3 and 5, wherein at least one of applying a first quantity of the sol and applying a second quantity of the sol occurs while the substrate is positioned in the ammonia atmosphere.

Embodiment 7 is the method of embodiment 6, wherein applying the sol includes decanting the sol over the substrate while rotating the substrate in the ammonia atmosphere.

Embodiment 8 is the method of any of embodiments 1-7, further comprising positioning the second coated substrate in the ammonia atmosphere to cure the second quantity of the sol to form a second supported gel comprising a second gel and the first gel supported by the substrate.

Embodiment 9 is the method of embodiment 8, wherein positioning the second coated substrate in the ammonia atmosphere further cures the first gel.

Embodiment 10 is the method of embodiment 8 or 9, wherein the second gel and the first gel together form a monolithic gel body, supported by the substrate.

Embodiment 11 is the method of any of embodiments 8-10, further comprising applying a third quantity of the sol to the second gel on the substrate to form a third coated substrate comprising the third quantity of sol and the second supported gel.

Embodiment 12 is the method of embodiment 11, further comprising positioning the third coated substrate in the ammonia atmosphere to cure the third quantity of the sol to form a third supported gel comprising a third gel supported by the second supported gel.

Embodiment 13 is the method of embodiment 12, wherein positioning the third coated substrate in the ammonia atmosphere further cures at least one of the first gel and the second gel.

Embodiment 14 is the method of embodiment 12 or 13, wherein the third coated substrate is positioned in the ammonia atmosphere for a greater period of time than at least one of the second coated substrate and the first coated substrate.

Embodiment 15 is the method of any of embodiments 12-14, wherein the first gel, the second gel and the third gel together form a monolithic gel body, supported by the substrate.

Embodiment 16 is the method of embodiment 10 or 15, further comprising removing the substrate from the monolithic gel body to form a self-supporting monolithic gel body.

Embodiment 17 is the method of any of embodiments 10, 15 and 16, wherein the substrate has a first dimension oriented in a direction and the monolithic gel body has a second dimension oriented in the direction, and wherein the ratio of the first dimension to the second dimension is no greater than 1.

Embodiment 18 is the method of any of embodiments 10 and 15-17, wherein the monolithic gel body includes a dimension that is at least 3 cm.

Embodiment 19 is the method of any of embodiments 1-18, wherein the applying steps and the positioning step occur simultaneously by maintaining the substrate in the ammonia atmosphere during the two applying steps.

Embodiment 20 is the method of any of embodiments 1-19, wherein applying the sol to the substrate, positioning the first coated substrate in the ammonia atmosphere, and applying the sol to the first coated substrate occur sequentially.

Embodiment 21 is the method of any of embodiments 1-20, wherein applying a second quantity of the sol to the first gel on the substrate occurs before the first gel is completely dry.

Embodiment 22 is a method for making a monolithic gel body, the method comprising:
  providing a substrate;
  providing a sol;
  providing an ammonia atmosphere;
  dipping the substrate in the sol;
  removing the substrate from the sol to form a first coated substrate comprising a first coating of sol on the substrate;
  positioning the first coated substrate in the ammonia atmosphere to cure the first coating of sol to form a first supported gel comprising a first gel supported by the substrate;
  dipping the first supported gel in the sol; and
  removing the first supported gel from the sol to form a second coated substrate comprising a second coating of sol on the first supported gel.

Embodiment 23 is the method of embodiment 22, further comprising controlling the rate at which at least one of the first coated substrate and the second coated substrate is removed from the sol to control the thickness of at least one of the first coating of sol and the second coating of sol.

Embodiment 24 is the method of embodiment 22 or 23, further comprising positioning the second coated substrate in the ammonia atmosphere to cure the second coating of sol to form a second supported gel comprising a second gel supported by the first supported gel.

Embodiment 25 is the method of embodiment 24, wherein positioning the second coated substrate in the ammonia atmosphere further cures the first gel.

Embodiment 26 is the method of embodiment 24 or 25, wherein the first gel and the second gel together form a monolithic gel body, supported by the substrate.

Embodiment 27 is the method of any of embodiments 24-26, further comprising:
  dipping the second supported gel in the sol; and
  removing the second supported gel from the sol to form a third coated substrate comprising a third coating of sol on the second supported gel.

Embodiment 28 is the method of embodiment 27, further comprising positioning the third coated substrate in the ammonia atmosphere to cure the third coating of sol to form a third supported gel comprising a third gel supported by the second supported gel.

Embodiment 29 is the method of embodiment 28, wherein the first gel, the second gel and the third gel together form a monolithic gel body, supported by the substrate.

Embodiment 30 is the method of embodiment 26 or 29, further comprising removing the substrate from the monolithic gel body to form a self-supporting monolithic gel body.

Embodiment 31 is the method of any of embodiments 26, 29 and 30, wherein the substrate has a first dimension oriented in a direction and the monolithic gel body has a second dimension oriented in the direction, and wherein the ratio of the first dimension to the second dimension is no greater than 1.

Embodiment 32 is a method for making a monolithic gel body, the method comprising:
  providing a substrate;
  providing a sol;
  providing an ammonia atmosphere; and
  positioning the substrate in the ammonia atmosphere while applying the sol onto the substrate to form a monolithic gel body by a layering process.

Embodiment 33 is the method of embodiment 32, wherein the monolithic gel body is supported by the substrate, and further comprising removing the substrate from the monolithic gel body to form a self-supporting monolithic gel body.

Embodiment 34 is the method of embodiment 32 or 33, wherein the substrate has a first dimension oriented in a direction and the monolithic gel body has a second dimension oriented in the direction, and wherein the ratio of the first dimension to the second dimension is no greater than 1.

Embodiment 35 is the method of any of embodiments 32-34, wherein applying the sol includes continuously applying the sol while positioning the substrate in the ammonia atmosphere.

Embodiment 36 is the method of any of embodiments 32-35, wherein applying the sol onto the substrate includes rotating the substrate while applying the sol.

Embodiment 37 is the method of embodiment 36, further comprising controlling the rate at which the substrate is rotated to control the homogeneity of the thickness of the layers of the monolithic gel body.

Embodiment 38 is the method of any of embodiments 32-37, wherein applying the sol includes decanting.

Embodiment 39 is the method of any of embodiments 32-37, wherein applying the sol includes applying droplets of sol onto the substrate.

Embodiment 40 is the method of embodiment 39, further comprising controlling the size of the droplets to control the thickness of each layer forming the monolithic gel body.

Embodiment 41 is the method of any of embodiments 1-40, wherein the sol is an acetate-stabilized zirconia sol.

The following working examples are intended to be illustrative of the present disclosure and not limiting.

EXAMPLES

Example 1

Formation of a Zirconia Gel Body by Dipping

In Example 1, a zirconia gel body was formed according to the method 200 illustrated in FIG. 2 and described above. A sol of nano-sized zirconia particles in aqueous acetic acid was provided (solids content ~8 vol-%, acetic acid content ~3 wt.-%, from 3M ESPE, St Paul, Minn.). A small plastic stick served as the substrate and was dipped into the sol to form a first coated substrate, and then suspended about 3 cm above an aqueous solution of ammonia (0.25 wt.-%, 5 mL) contained in a plastic tube 2 cm diameter and 9 cm in height (i.e., the stick was positioned such that the stick extended across the top opening of the tube). The ammonia vapor reacted with the acetic acid and the clear sol turned into a turbid gel (i.e., a supported gel). After 5 minutes, the gel was dipped into the sol again to form a second coated substrate. The gel body formed as a turbid bead having an elongated shape. This process was repeated and successive layers increased the size of the gel body.

After about 2 hours of iteratively dipping and curing with ammonia, the gel had reached the desired size (in this case ~2 cm in length and 7 mm in diameter) and displayed a droplet shape. The gel was kept in the ammonia vapor overnight and then dried in air for 1 day, yielding a transparent and completely dry gel body having adequate strength for handling.

Example 2

Formation of a Zirconia Gel Body Using Rotation

In Example 2, a zirconia gel body was formed according to the method 300 illustrated in FIG. 3 and described above. A sol of nano-sized zirconia particles in aqueous acetic acid was provided (solids content ~8 vol-%, acetic acid content ~3 wt.-%, from 3M ESPE, St Paul, Minn.). A small plastic stick served as the substrate and was attached to a mechanical stirring unit, which was oriented horizontally and rotated at a speed of about 60-120 rpm. The tip of the rotating stick was positioned about 1 cm above a plastic tube (i.e., positioned such that the stick extended across the top opening of the tube) of 2 cm diameter and 9 cm in height filled entirely with an aqueous solution of ammonia (0.25 wt.-%, about 30 mL). Drop by drop, sol was poured over the turning tip by letting it run off a plastic spatula. The gel body formed as a turbid bead of approximately spherical shape. This process was continued and successive layers increased the size of the gel body until it reached the desired size (in this case ~1 cm in diameter, which took about an hour. The gel body was held in position over the ammonia solution for 1 day without rotating it. The resulting completely dry gel body possessed adequate strength for handling.

The embodiments described above and illustrated in the figures are presented by way of example only and are not intended as a limitation upon the concepts and principles of the present disclosure. As such, it will be appreciated by one having ordinary skill in the art that various changes in the elements and their configuration, arrangement, or sequence are possible without departing from the spirit and scope of the present disclosure. Various features and aspects of the present disclosure are set forth in the following claims.

What is claimed is:

1. A method for making a monolithic gel body, the method comprising:
   providing a substrate;
   providing a sol;
   applying a first quantity of the sol to the substrate to form a first coated substrate;
   positioning the first coated substrate in an ammonia atmosphere to cure the first quantity of sol to form a first supported gel comprising a first gel supported by the substrate;
   applying a second quantity of the sol to the first supported gel to form a second coated substrate comprising the second quantity of sol and the first supported gel, and
   positioning the second coated substrate in the ammonia atmosphere to cure the second quantity of the sol to form a second supported gel comprising a second gel and the first gel supported by the substrate.

2. The method of claim 1, wherein at least one of applying a first quantity of the sol and applying a second quantity of the sol includes decanting the sol.

3. The method of claim 2, wherein decanting the sol includes decanting the sol dropwise.

4. The method of claim 1, wherein at least one of applying a first quantity of the sol and applying a second quantity of the sol includes dipping the substrate into the sol.

5. The method of claim 1, wherein at least one of applying a first quantity of the sol and applying a second quantity of the sol occurs while rotating the substrate.

6. The method of claim 1, wherein at least one of applying a first quantity of the sol and applying a second quantity of the sol occurs while the substrate is positioned in the ammonia atmosphere.

7. The method of claim 6, wherein applying the sol includes decanting the sol over the substrate while rotating the substrate in the ammonia atmosphere.

8. The method of claim 1, wherein positioning the second coated substrate in the ammonia atmosphere further cures the first gel.

9. The method of claim 1, wherein the second gel and the first gel together form a monolithic gel body, supported by the substrate.

10. The method of claim 1, further comprising:
    applying a third quantity of the sol to the second gel on the substrate to form a third coated substrate comprising the third quantity of sol and the second supported gel, and
    positioning the third coated substrate in the ammonia atmosphere to cure the third quantity of the sol to form a third supported gel comprising a third gel supported by the second supported gel.

11. The method of claim 10, wherein positioning the third coated substrate in the ammonia atmosphere further cures at least one of the first gel and the second gel.

12. The method of claim 10, wherein the third coated substrate is positioned in the ammonia atmosphere for a greater period of time than at least one of the second coated substrate and the first coated substrate.

13. The method of claim 10, wherein the first gel, the second gel and the third gel together form a monolithic gel body, supported by the substrate.

14. The method of claim 9, further comprising removing the substrate from the monolithic gel body to form a self-supporting monolithic gel body.

15. The method of claim 9, wherein the substrate has a first dimension oriented in a direction and the monolithic gel body has a second dimension oriented in said direction, and wherein the ratio of the first dimension to the second dimension is no greater than 1.

16. The method of claim 9, wherein the monolithic gel body includes a dimension that is at least 3 cm.

17. The method of claim 1, further comprising optionally drying the first supported gel, wherein applying a second quantity of the sol to the first supported gel on the substrate occurs before the first supported gel is completely dry.

18. The method of claim 1, wherein the sol is an acetate-stabilized zirconia sol.

19. The method of claim 1, wherein the applying steps and the positioning steps occur simultaneously by maintaining the substrate in the ammonia atmosphere during the two applying steps.

20. The method of claim 1, wherein applying a first quantity of the sol to the substrate, positioning the first coated substrate in the ammonia atmosphere, applying a second quantity of the sol to the first supported gel, and positioning the second coated substrate in the ammonia atmosphere occur sequentially.

21. A method for making a monolithic gel body, the method comprising:
    providing a substrate;
    providing a sol;
    providing an ammonia atmosphere; and
    positioning the substrate in the ammonia atmosphere while applying the sol onto the substrate to form a monolithic gel body layer-by-layer by at least partially curing each sol layer in the ammonia atmosphere as it is formed.

* * * * *